(12) United States Patent
Davies et al.

(10) Patent No.: US 7,749,716 B2
(45) Date of Patent: Jul. 6, 2010

(54) METHODS OF DETECTING A FRAGMENT OF NEUROSECRETORY PROTEIN VGF FOR DIAGNOSING ALZHEIMER'S DISEASE

(75) Inventors: Huw Alun Davies, Surrey (GB); Kaj Blennow, Molndal (SE); James McGuire, Virum (DK); Vladimir Podust, Fremont, CA (US); Anja Hviid Simonsen, Frederiksberg (DK)

(73) Assignee: Vermilllion, Inc., Fremont, CA (US)

( * ) Notice: Subject to any disclaimer, the term of this patent is extended or adjusted under 35 U.S.C. 154(b) by 0 days.

(21) Appl. No.: 11/452,477

(22) Filed: Jun. 13, 2006

(65) Prior Publication Data
US 2007/0015221 A1 Jan. 18, 2007

Related U.S. Application Data

(60) Provisional application No. 60/691,637, filed on Jun. 16, 2005.

(51) Int. Cl.
G01N 33/543 (2006.01)
(52) U.S. Cl. ..................... 435/7.1
(58) Field of Classification Search ............. None
See application file for complete search history.

(56) References Cited

U.S. PATENT DOCUMENTS

| 5,880,116 | A | * | 3/1999 | Vigo-Pelfrey | 514/178 |
| 6,225,047 | B1 | * | 5/2001 | Hutchens et al. | 435/5 |
| 2006/0240561 | A1 | * | 10/2006 | Yalkinoglu et al. | 436/86 |

FOREIGN PATENT DOCUMENTS

| CA | 2 446 886 | * | 10/2002 |
| WO | 02/082075 | * | 10/2002 |
| WO | 2004/019043 | * | 3/2004 |

OTHER PUBLICATIONS

Rachakonda et al. (Cell Res. Oct. 2004;14(5):349-360.*
Pleines et al, 2001, J. Neurotrauma 18:491-498.*
Blennow et al. Chromogranin A in cerebrospinal fluid: a biochemical marker for synaptic degeneration in Alzheimer's disease? Dementia, vol. 6, (1995), pp. 306-311.
Carrett et al. "A panel of cerebrospinal fluid potential biomarkers for the diagnosis of Alzheimer's disease" Proteomics vol. 3, (Aug. 2003), pp. 1486-1494.
Davidson et al. "Proteome analysis of cerebrospinal fluid proteins in Alzheimer patients" Clinical Nueroscience and Nueropathology (Apr. 2002), vol. 13, No. 5, pp. 611-615.
Elovaara "Proteins in serum and cerebrospinal fluid in demented patients with Down's syndrome" Acta Nuerological Scand., vol. 69, (1984) pp. 302-305.
Harigaya et al. "Alpha 1-antichymotrypsin level in cerebrospinal fluid is closely associated with late onset Alzheimer's disease" Internal Medicine, vol. 34, No. 6 (Jun. 1995), pp. 481-484.
Hoekman, et al. "The significance of beta-2 microglobulin in clinical medicine" Neth. J. Med. vol. 28, (1985) pp. 551-557.
Iqbal et al. "Mechanisms of nuerofibrillary degeneration and the formation of nuerofibrillary tangles" J. Neural Transm vol. 53, (1998) pp. 169-180.
Kudo et al. "Alzheimer disease: correlation of cerebro-spinal fluid and brain ubiquitin levels" Brain Research, vol. 639, (Mar. 1994), pp. 1-7.
Levy et al. "Codeposition of cystatin C with amyloid-β protein in the brain of Alzheimer disease patients", Journal of Neuropathology and Experimental Nuerology, vol. 60, No. 1 (Jan. 2001) pp. 94-104.
Lüthi, U., "Proteolytic Enzymes as Therapeutic Targets," ESBAtech, 2002, 5 pp.
Mares, J., et al., "Use of Cystatin C Determination in Clinical Diagnostics," Biomed. Papers, 2003, vol. 147., No. 2, pp. 177-180.
Matsubara et al. "α1-Antichymotrypsin as a possible biochemical marker for Alzheimer-type dementia" Annals of Neurology vol. 28, No. 4 (Oct. 1990) pp. 561-567.
Merched et al. "Apolipoprotein E, transthyretin and actin in the CSF of Alzheimer's patients: relation with the senile plaques and cytoskeleton biochemistry" FEBS Letters; vol. 425, No. 2, (1998) pp. 225-228.
Popovic, T. et al., "Different Forms of Human Cycstatin C." Biol. Chem., 1990, vol. 371, pp. 575-580.
Potter et al. "The inflammation-induced pathological chaperones ACT and apo-E are necessary catalysts of Alzheimer amyloid formation" Neurobology of Aging, vol. 22, (2001) pp. 923-930.
Riisøen, "Reduced prealbumin (transthyretin) in CSF of severely demented patients with Alzheimer's disease" Acta Nuerolgoical Scand. vol. 78, (1988) pp. 455-459.
Serot et al. "Cerebrospinal fluid transthyretin: aging and late onset Alzheimer's disease", J Neurol Neurosurg Psychiatry; vol. 63 (Oct. 1997) pp. 506-508.
Skoog et al. "A population study on blood-brain barrier function in 85-year-olds" Neurology vol. 50, (1998) pp. 961-971.
Tsuzuki et al. "Transthyretin binds amyloid β peptides, Aβ1-42 and Aβ1-40 to form complex in the autopsied human kidney—possible role of transthyretin for Aβ sequestration" Nueroscience Letters, vol. 281. (2000) pp. 171-174.
Wang et al. "Alzheimer's disease: paired helical filament immunoreactivity in cerebrospinal fluid" Acta Neuropathol vol. 82, No. 1, (1991) pp. 6-12.

* cited by examiner

*Primary Examiner*—Daniel E. Kolker
(74) *Attorney, Agent, or Firm*—Edwards Angell Palmer & Dodge LLP; Peter F. Corless; Jonathan M. Sparks

(57) ABSTRACT

The present invention provides a neurosecretory protein VGF peptide useful in qualifying Alzheimer's disease status in a patient. In particular, this peptide and modified forms thereof may be used to classify a subject sample as Alzheimer's disease or non-Alzheimer's disease. The peptide biomarker can be detected by SELDI mass spectrometry.

15 Claims, 1 Drawing Sheet

METHODS OF DETECTING A FRAGMENT OF NEUROSECRETORY PROTEIN VGF FOR DIAGNOSING ALZHEIMER'S DISEASE

This application claims the benefit of priority of U.S. provisional application 60/691,637, filed Jun. 16, 2005, the entire disclosure of which is hereby incorporated herein by reference.

FIELD OF THE INVENTION

The invention relates generally to clinical diagnostics.

BACKGROUND OF THE INVENTION

Alzheimer's Disease is a progressive neurodegenerative disorder that leads to the death of brain cells that cannot be replaced once lost. The neuropathology is characterized by the presence of amyloid plaques, neurofibrillary tangles, synaptic loss and selective neuronal cell death. The plaques are a result of abnormal levels of extracellular amyloid beta peptide (A$\beta$) while the tangles are associated with the presence of intracellular hyperphosphorylated tau protein. Symptoms first manifest clinically with a decline in memory followed by deterioration in cognitive function and normal behavior. Age is the single most prominent risk factor with the incidence doubling every five years from at the age of 65. Prevalence studies estimated that in 2000 the number of persons with AD in the US alone was 4.5 million with numbers expected to increase almost 3 fold in the next 50 years due to the rapid growth of the oldest age groups. The increasing number of dementia patients in the developed world will place an enormous burden on society and the health care systems.

Despite significant advances in the understanding of AD pathogenesis there are no drugs that exhibit profound disease-modifying effects. Although great efforts are being made to develop future classes of drugs to slow disease progression, current therapy, typified by the acetylcholinesterase inhibitors, is mainly limited to alleviating symptoms (Davis R E et al. (1995) *Arzneimittelforschung,* 45:425-431). Early diagnosis is a prerequisite for early treatment and will be of even greater significance if drugs aimed at slowing neurodegeneration show a clinical effect.

Current criteria for the clinical diagnosis of AD are largely dependent on the exclusion of other dementias and include neuropsychological testing and neuroimaging, where possible (McKhann G. et al., (1984) *Neurology* 34:939-944). Although reasonably high accuracy rates of 80-90% using clinical criteria have been reported (Kosunen O et al., (1996) *Acta Neuropathol* 91:185-193) these studies have been conducted by specialized centers typically diagnosing patients in the later stages of disease. Diagnostic accuracy within routine clinical practice is probably much lower, particularly during mild or pre-symptomatic stages of the disease. An unambiguous diagnosis of the disease is currently only possible by examination of brain tissue pathology and is not a clinically feasible process.

Several candidate biomarkers have been discovered in cerebrospinal fluid (CSF) such as A$\beta$1-42 and tau, which are the major components of amyloid plaques and neurofibrillary tangles, respectively. These tests have been commercialized and are used routinely in parts of Europe for research and diagnostic purposes. The diagnostic performance of these biomarkers is not optimal, however, especially with respect to specificity against other dementias (Blennow K & Hampel H, (2003) *Lancet Neurol.* 2:605-613). Many other markers have been proposed in both serum and CSF and include amyloid precursor protein, apoE, isoprostanes (markers of lipid oxidation) and homocysteine. Whether these can be used as diagnostic markers has yet to be confirmed (Frank R A. et al. (2003) *Neurobiol of Aging* 24:521-536).

Therefore, there is an unmet need for simple biochemical tests that can detect AD at an early stage, monitor progression of the disease, and discriminate between AD, normal subjects, non-AD dementias and other neurological disorders.

BRIEF SUMMARY OF THE INVENTION

The present invention fills these needs by providing novel biomarkers and combinations of biomarkers useful for diagnosing Alzheimer's disease, as well as methods and kits for using the biomarkers to diagnose Alzheimer's disease.

More specifically, in one embodiment, the invention provides a method for qualifying Alzheimer's disease status in a subject comprising measuring at least one biomarker in a biological sample from the subject, wherein the at least one biomarker is VGF peptide-1, shown in Table 1 (i.e., M6608); and correlating the measurement with Alzheimer's disease status. In another related embodiment, the at least one biomarker is a modified form of the VGF peptide-1, e.g., a post-translationally modified form such as a further truncated or glycosylated form.

The invention provides several different methods of measuring biomarkers useful for qualifying Alzheimer's disease status. For example, in one embodiment of the invention, at least one biomarker is measured by capturing the biomarker on an adsorbent surface of a SELDI probe and detecting the captured biomarkers by laser desorption-ionization mass spectrometry. In one embodiment, the adsorbent comprises an ion-exchange adsorbent. In a related embodiment, the ion-exchange adsorbent is a Q10 Biochip (Ciphergen Biosystems, Inc.). In another embodiment, the adsorbent comprises a biospecific adsorbent.

In some embodiments of the invention, the biomarkers of the invention, e.g., the VGF peptide of Table 1, may be measured by a method other than mass spectrometry, e.g., by methods that do not involve or, alternatively, do not require a measurement of the mass of the biomarker to detect or quantify the biomarker's presence in a sample. For example, the biomarkers of the invention may be detected by an immunoassay. In one embodiment, the invention provides an immunoassay comprising an antibody specific for VGF peptide-1. For example, the N-terminus of the VGF peptide-1 may be specifically detected. In one embodiment, the invention provides an immunoassay which utilizes an antibody specific for VGF peptide-1. In a related embodiment, the antibodies recognized glycosylated or otherwise post-translationally modified forms of VGF peptide-1.

In a preferred embodiment, the invention provides methods of detecting VGF peptide-1 in bodily fluids, including cerebral spinal fluid ("CSF").

In a related embodiment, the correlating of biomarker expression with Alzheimer's disease status is performed by a software classification algorithm.

In yet another embodiment, the Alzheimer's disease status is selected from Alzheimer's disease and non-Alzheimer's disease. The invention further provides methods of managing subject treatment based on the status. In one embodiment, the invention further comprises reporting the subject's Alzheimer's disease status to the subject. In a related embodiment, the invention further comprises recording the Alzheimer's disease status on a tangible medium.

For example, if the measurement correlates with Alzheimer's disease, then managing subject treatment comprises monitoring the subject for symptoms of disease progression and/or regression and/or providing therapeutic care for the subject. In yet another embodiment, the diagnostic methods of the invention further comprise measuring at VGF peptide-1 after subject management and correlating the measurement with disease progression.

In a related embodiment, the invention provides a method for determining the course of Alzheimer's disease comprising the step of measuring, at a first time, at least one biomarker in a biological sample from a subject, wherein the at least one biomarker is VGF peptide-1; measuring one or more of the selected biomarkers in a biological sample from the subject at a second time; and comparing the first measurement to the second measurement to determine the course of the Alzheimer's disease. In a related embodiment, the second measurement in the method occurs after subject management. In a further related embodiment, the method for determining the course of Alzheimer's disease status in a subject comprises reporting the course of disease status and/or recording the course of disease status on a tangible medium.

In another embodiment, subject management comprises administering a cholinesterase inhibitor to the subject.

In another embodiment, the invention provides a method comprising measuring at least one biomarker in a sample from a subject, wherein the at least one biomarker is VGF peptide-1.

In one embodiment, the invention additionally provides a purified VGF peptide-1. In another embodiment, the invention provides a composition comprising a biospecific capture reagent bound to, or capable of binding to, VGF peptide-1. In a related embodiment, the biospecific capture reagent is an antibody.

In yet another embodiment, the invention provides kits comprising an article of manufacture which in turn comprises a solid support and at least one capture reagent attached thereto, wherein the capture reagent binds VGF peptide-1. In another related embodiment, the capture reagent is one which binds VGF peptide-1 with high specificity and selectivity, such as a monoclonal antibody specific for VFG peptide-1. The kits also comprise instructions for using the solid support to measure selected biomarker(s) and to correlate the measurement(s) with Alzheimer's disease status. In one embodiments, the kit further comprises instructions for using the solid support to measure VGF peptide-1. In yet another embodiment, the solid support comprising the capture reagent is a SELDI probe. In still another embodiment, the capture reagent or reagents comprise a hydrophobic adsorbent. In yet another embodiment, the kit comprises a container comprising VGF peptide-1. In another related embodiment, the capture reagent(s) of the kit comprises an anion exchange chromatography adsorbent.

In yet another embodiment, the invention provides a kit comprising an article of manufacture, where the article of manufacture comprises a solid support and at least one capture reagent attached thereto, and wherein the capture agent includes the VGF peptide-1 biomarker, and where the kit further comprises a container comprising VGF peptide-1. In yet another embodiment, the solid support comprising at least one attached capture reagent is a SELDI probe.

In yet another embodiment, the invention provides a software product comprising a code that accesses data attributed to a sample, wherein the data comprises the measurement of at least one biomarker in the sample, where the at least one biomarker includes VGF peptide; and wherein the software further comprises a code that executes a classification algorithm that classifies the Alzheimer's disease status of the sample as a function of the measurement. In a related embodiment, the classification algorithm classifies the Alzheimer's disease status of the sample as a function of the measurement of one or more biomarkers, wherein said one or more biomarkers includes VGF peptide-1.

The invention additionally provides a method comprising the step of detecting VGF peptide-1 by mass spectrometry or immunoassay.

In yet another embodiment, the invention provides a method comprising the step of communicating to a subject a diagnosis relating to Alzheimer's disease status determined from the correlation of biomarkers in a sample from the subject, wherein said biomarkers include VGF peptide-1. In a related embodiment, the diagnosis is communicated to the subject via a computer-generated medium.

In yet another embodiment, the invention provides a method for identifying a compound that interacts with the VGF peptide-1 biomarker, wherein said method comprises contacting said biomarker with a test compound, and determining whether the test compound interacts with said biomarker.

In another embodiment, the invention provides a method for modulating the concentration of a biomarker in a cell, wherein said biomarker is the VGF peptide-1, and wherein said method comprises the step of contacting said cell with an antisense or interfering RNA molecule, wherein said antisense or interfering RNA molecule inhibits expression of VGF peptide-1 in the cell.

In another embodiment, the invention provides a method of treating a condition in a subject associated with the overexpression of a biomarker in a cell, wherein said biomarker is VGF peptide-1, and wherein said method comprises administering to the subject a therapeutically effective amount of an antisense or interfering RNA molecule, wherein said antisense or RNA interfering molecule inhibits expression of said biomarker in the cell. In a related embodiment, the treated condition is Alzheimer's disease.

In another embodiment, the invention provides a method for modulating the concentration of the VGF peptide-1 in a cell or tissue, comprising the steps of contacting the cell or tissue with a protease inhibitor, wherein said protease inhibitor prevents cleavage of native VGF protein at the positions which lead to the production of VFG peptide-1.

In another embodiment, the invention provides a method of treating a condition in a subject, wherein said method comprises administering to a subject a therapeutically effective amount of a protease inhibitor which prevents cleavage of native VGF protein. In a related embodiment, the condition is Alzheimer's disease.

DETAILED DESCRIPTION OF THE INVENTION

I. Introduction

Figure 1:
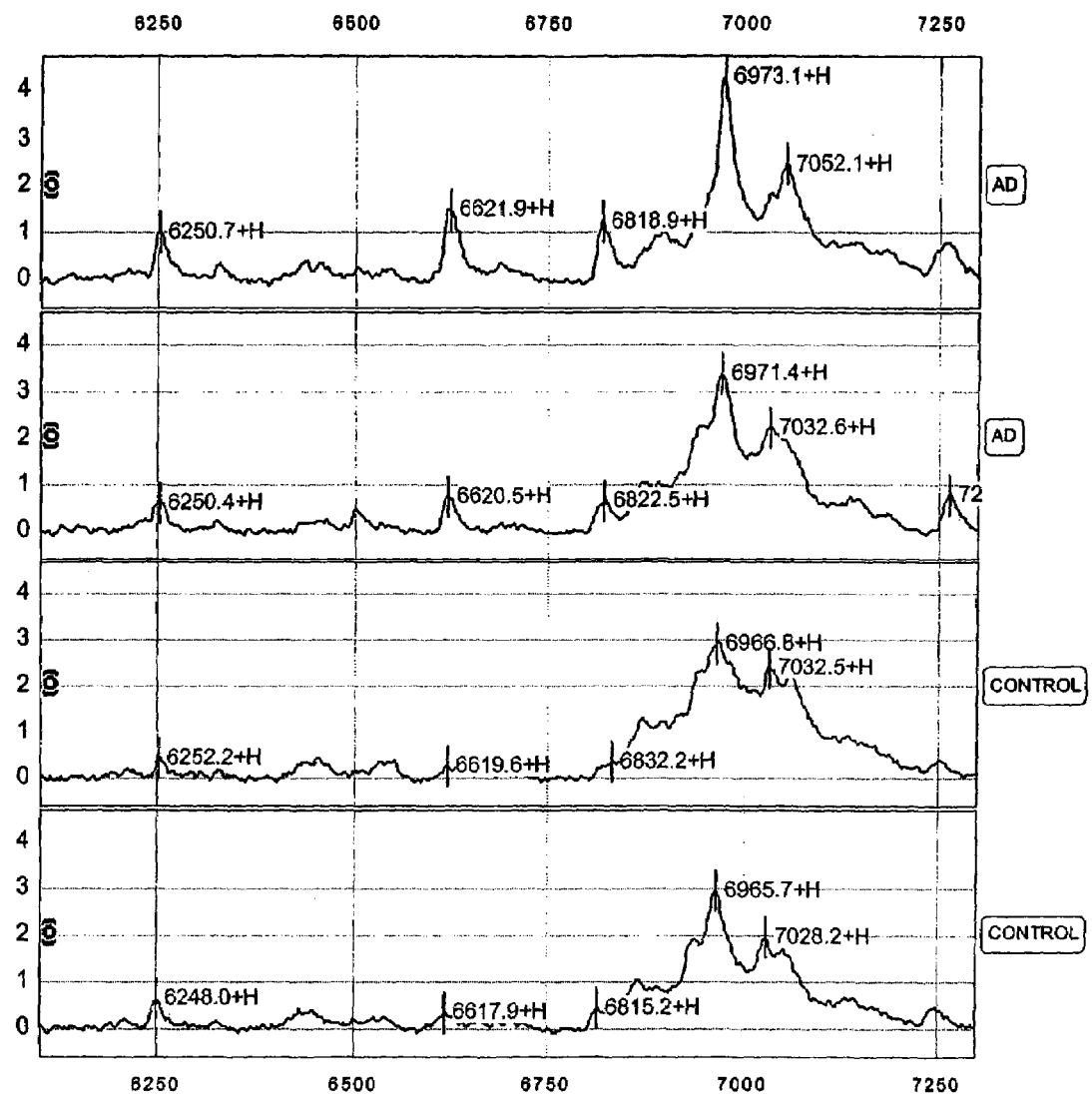
FIG. 1 shows a representative mass spectra for the VGF peptide biomarker.

A biomarker is an organic biomolecule which is differentially present in a sample taken from a subject of one phenotypic status (e.g., having a disease) as compared with another phenotypic status (e.g., not having the disease). A biomarker is differentially present between different phenotypic statuses if the mean or median expression level of the biomarker in the different groups is calculated to be statistically significant. Common tests for statistical significance include, among others, t-test, ANOVA, Kruskal-Wallis, Wilcoxon, Mann-Whitney and odds ratio. Biomarkers, alone or in combination, provide measures of relative risk that a subject belongs to one phenotypic status or another. Therefore, they are useful as markers for disease (diagnostics), therapeutic effectiveness of a drug (theranostics) and drug toxicity.

II. Biomarkers for Alzheimer's Disease

This invention provides polypeptide-based biomarkers that are differentially present in subjects having Alzheimer's disease, in particular, Alzheimer's disease versus normal (non-Alzheimer's disease). The biomarkers are characterized by mass-to-charge ratio as determined by mass spectrometry, by the shape of their spectral peak in time-of-flight mass spectrometry and by their binding characteristics to adsorbent surfaces. These characteristics provide one method to determine whether a particular detected biomolecule is a biomarker of this invention. These characteristics represent inherent characteristics of the biomolecules and not process limitations in the manner in which the biomolecules are discriminated. In one aspect, this invention provides these biomarkers in isolated form.

The biomarkers were discovered using SELDI technology employing ProteinChip arrays from Ciphergen Biosystems, Inc. (Fremont, Calif.) ("Ciphergen"). CSF samples were collected from subjects diagnosed with Alzheimer's disease and subjects diagnosed as normal. The samples were applied to SELDI biochips and spectra of polypeptides in the samples were generated by time-of-flight mass spectrometry on a Ciphergen PBSII mass spectrometer. The spectra thus obtained were analyzed by Ciphergen Express™ Data Manager Software with Biomarker Wizard and Biomarker Pattern Software from Ciphergen Biosystems, Inc. The mass spectra for each group were subjected to scatter plot analysis. A Mann-Whitney test analysis was employed to compare Alzheimer's disease and control groups for each protein cluster in the scatter plot, and proteins were selected that differed significantly (p<0.0001) between the two groups. This method is described in more detail in the Example Section.

An Alzheimer's disease biomarker thus discovered and identified is presented in Table 1. The biomarker, VGF peptide-1, is elevated in Alzheimer's disease compared with normal. The VGF peptide biomarker of Table 1 is a fragment of the neurosecretory protein VGF. Full length VGF is a 616 amino acid protein (SwissProt Accession No. 015240). VGF Peptide-1 has the following amino acid sequence: SQEET-PGHRR KEAEGTEEGG EEEDDEEMDP QTIDSLIELS TKLHLPADDV VSIIEEVEE (SEQ ID NO. 1). This corresponds to amino acids 421-479 of the full length protein. The relationship of VGF peptide-1 to the full-length VGF protein is described in more detail in the Example section.

TABLE 1

| Marker ID, m/z | P-Value | ROC AUC | Up or down regulated in Alzheimer's disease | ProteinChip ® assay |
|---|---|---|---|---|
| VGF Peptide-1 M6620.0 (predicted mass: 6621.98) | <0.0001 | 0.7160 | Up-regulated | Q10 SPA (anion exchange surface, pH 9) (Also previously detected under same conditions at 6608 D, which is within the margin of error for mass measurement with this instrument.) |

The biomarkers of this invention are characterized by their mass-to-charge ratio as determined by mass spectrometry. The mass-to-charge ratio of each biomarker is provided in Table 1 after the "M." Thus, for example, M6620.0 has a measured mass-to-charge ratio of 6620.0. The peak corresponding to the VGF peptide was previously observed as an approximately 6608 m/z Alzheimer's disease biomarker in U.S. Provisional Patent App. No. 60/673,277, entitled, "Saposin D and FAM 3C are Biomarkers for Alzheimer's Disease; and in PCT/US2004/037994, filed 6 Nov. 2004, entitled, "Biomarkers for Alzheimer's Disease" (International Patent Publication WO 2005/047484). The mass-to-charge ratios were determined from mass spectra generated on a Ciphergen Biosystems, Inc. PBS II mass spectrometer. This instrument has a mass accuracy of about +/−0.15 percent. Additionally, the instrument has a mass resolution of about 400 to 1000 m/dm, where m is mass and dm is the mass spectral peak width at 0.5 peak height. The mass-to-charge ratio of the biomarkers was determined using Biomarker Wizard™ software (Ciphergen Biosystems, Inc.). Biomarker Wizard assigns a mass-to-charge ratio to a biomarker by clustering the mass-to-charge ratios of the same peaks from all the spectra analyzed, as determined by the PBSII, taking the maximum and minimum mass-to-charge-ratio in the cluster, and dividing by two. Accordingly, the masses provided reflect these specifications. Further accuracy in the determination of masses may be obtained by calibrating the instrument using peaks whose identity has been determined (i.e., peaks corresponding to peptides of known amino acid sequence).

The biomarkers of this invention are further characterized by the shape of their spectral peak in time-of-flight mass spectrometry. Mass spectra showing the shape of peak(s) representing the VGF peptide biomarker are presented in FIG. 1.

The biomarkers of this invention are further characterized by their binding properties on chromatographic surfaces. The "ProteinChip assay" column in Table 1 refers to the type of biochip to which the biomarker binds. Specifically, VGF peptide binds to anion exchange adsorbents (e.g., the Ciphergen® Q10 ProteinChip® array) at pH 9.0. "SPA" refers to sinapinic acid, an agent used as an energy absorbing matrix in conjunction with the ProteinChip arrays.

The method by which the identity of the VGF peptide was determined is described in the Example Section. For biomarkers whose identify has been determined, the presence of the biomarker can be determined by other methods known in the art.

The preferred biological source for detection of the biomarkers is cerebrospinal fluid ("CSF"). However, the biomarkers may be present in other bodily fluids, e.g., serum, blood, or urine.

The biomarkers of this invention are biomolecules. Accordingly, this invention provides these biomolecules in isolated form. The biomarkers can be isolated from biological fluids, such as CSF. They can be isolated by any method known in the art, based on both their mass and their binding characteristics. For example, a sample comprising the biomolecules can be subject to chromatographic fractionation, as described herein, and subject to further separation by, e.g., acrylamide gel electrophoresis. Knowledge of the identity of the biomarker also allows their isolation by immunoaffinity chromatography.

A group of researchers (Yalkinoglu et al.) has independently disclosed an internal fragment of VGF as a biomarker in CSF for Alzheimer's disease (International Publication Number WO 2004/019043, published Mar. 4, 2004). The publication indicates that the biomarker was found using SELDI technology. However, the publication indicates that VGF fragment has a mass of 4.823 kD and corresponds about to amino acids 378-398 of full-length VGF. Therefore, it is a different fragment than VGF peptide-1 of this invention, which has a measured mass of about 6620 Da and corresponds to amino acids 421-479 of VGF.

III. Biomarkers and Different Forms of a Protein

Proteins frequently exist in a sample in a plurality of different forms. These forms can result from either or both of pre- and post-translational modification. Pre-translational modified forms include allelic variants, splice variants and RNA editing forms. Post-translationally modified forms include forms resulting from proteolytic cleavage (e.g., cleavage of a signal sequence or fragments of a parent protein), glycosylation, phosphorylation, lipidation, oxidation, methylation, cysteinylation, sulphonation and acetylation. When detecting or measuring a protein in a sample, the ability to differentiate between different forms of a protein depends upon the nature of the difference and the method used to detect or measure. For example, an immunoassay using a monoclonal antibody will detect all forms of a protein containing the eptiope and will not distinguish between them. However, a sandwich immunoassay that uses two antibodies directed against different epitopes on a protein will detect all forms of the protein that contain both epitopes and will not detect those forms that contain only one of the epitopes. In diagnostic assays, the inability to distinguish different forms of a protein has little impact when the forms detected by the particular method used are equally good biomarkers as any particular form. However, when a particular form (or a subset of particular forms) of a protein is a better biomarker than the collection of different forms detected together by a particular method, the power of the assay may suffer. In this case, it is useful to employ an assay method that distinguishes between forms of a protein and that specifically detects and measures a desired form or forms of the protein. Distinguishing different forms of an analyte or specifically detecting a particular form of an analyte is referred to as "resolving" the analyte.

Mass spectrometry is a particularly powerful methodology to resolve different forms of a protein because the different forms typically have different masses that can be resolved by mass spectrometry. Accordingly, if one form of a protein is a superior biomarker for a disease than another form of the biomarker, mass spectrometry may be able to specifically detect and measure the useful form where traditional immunoassay fails to distinguish the forms and fails to specifically detect to useful biomarker.

One useful methodology combines mass spectrometry with immunoassay. First, a biosepcific capture reagent (e.g., an antibody, aptamer or Affibody that recognizes the biomarker and other forms of it) is used to capture the biomarker of interest. Preferably, the biospecific capture reagent is bound to a solid phase, such as a bead, a plate, a membrane or an array. After unbound materials are washed away, the captured analytes are detected and/or measured by mass spectrometry. (This method also will also result in the capture of protein interactors that are bound to the proteins or that are otherwise recognized by antibodies and that, themselves, can be biomarkers.) Various forms of mass spectrometry are useful for dectecting the protein forms, including laser desorption approaches, such as traditional MALDI or SELDI, and electrospray ionization.

Thus, when reference is made herein to detecting a particular protein or to measuring the amount of a particular protein, it means detecting and measuring the protein with or without resolving various forms of protein. For example, the step of "measuring VGF peptide-1" includes measuring a polypeptide whose amino acid sequence corresponds to SEQ ID NO: 1, by means that do not differentiate between various forms of the protein in a sample (e.g., certain immunoassays) as well as by means that differentiate some forms from other forms or that measure a specific form of the protein (e.g., mass spectrometry). In contrast, when it is desired to measure a particular form or forms of a protein (e.g., any and/or all of M6620 and forms of M6620 modified by phosphorylation, glycosylation, etc.) the particular form or forms are specified. For example, "measuring M6620" means measuring a polypeptide having apparent molecular weight of 6620 Da that, therefore, distinguishes M6620 from other forms of VGF peptide-1.

IV. Detection of Biomarkers for Alzheimer's Disease

The biomarkers of this invention can be detected by any suitable method. Detection paradigms that can be employed to this end include optical methods, electrochemical methods (voltametry and amperometry techniques), atomic force microscopy, and radio frequency methods, e.g., multipolar resonance spectroscopy. Illustrative of optical methods, in addition to microscopy, both confocal and non-confocal, are detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

In one embodiment, a sample is analyzed by means of a biochip. Biochips generally comprise solid substrates and have a generally planar surface, to which a capture reagent (also called an adsorbent or affinity reagent) is attached. Frequently, the surface of a biochip comprises a plurality of addressable locations, each of which has the capture reagent bound there.

Protein biochips are biochips adapted for the capture of polypeptides. Many protein biochips are described in the art. These include, for example, protein biochips produced by Ciphergen Biosystems, Inc. (Fremont, Calif.), Zyomyx (Hayward, Calif.), Invitrogen (Carlsbad, Calif.), Biacore (Uppsala, Sweden) and Procognia (Berkshire, UK). Examples of such protein biochips are described in the following patents or published patent applications: U.S. Pat. No. 6,225,047 (Hutchens & Yip); U.S. Pat. No. 6,537,749 (Kuimelis and Wagner); U.S. Pat. No. 6,329,209 (Wagner et al.); PCT International Publication No. WO 00/56934 (Englert et al.); PCT International Publication No. WO 03/048768 (Boutell et al.); U.S. Pat. No. 6,902,897 (Tweedie et al.) and U.S. Pat. No. 5,242,828 (Bergstrom et al.).

Detection by Mass Spectrometry

In a preferred embodiment, the biomarkers of this invention are detected by mass spectrometry, a method that employs a mass spectrometer to detect gas phase ions. Examples of mass spectrometers are time-of-flight, magnetic sector, quadrupole filter, ion trap, ion cyclotron resonance, electrostatic sector analyzer and hybrids of these.

In a further preferred method, the mass spectrometer is a laser desorption/ionization mass spectrometer. In laser desorption/ionization mass spectrometry, the analytes are placed on the surface of a mass spectrometry probe, a device adapted to engage a probe interface of the mass spectrometer and to present an analyte to ionizing energy for ionization and introduction into a mass spectrometer. A laser desorption mass spectrometer employs laser energy, typically from an ultraviolet laser, but also from an infrared laser, to desorb analytes from a surface, to volatilize and ionize them and make them available to the ion optics of the mass spectrometer. The analyis of proteins by LDI can take the form of MALDI or of SELDI. The analyis of proteins by LDI can take the form of MALDI or of SELDI.

Laser desorption/ionization in a single TOF instrument typically is performed in linear extraction mode. Tandem mass spectrometers can employ orthogonal extraction modes.

SELDI

A preferred mass spectrometric technique for use in the invention is "Surface Enhanced Laser Desorption and Ionization" or "SELDI," as described, for example, in U.S. Pat. No. 5,719,060 and No. 6,225,047, both to Hutchens and Yip. This refers to a method of desorption/ionization gas phase ion spectrometry (e.g., mass spectrometry) in which an analyte (here, one or more of the biomarkers) is captured on the surface of a SELDI mass spectrometry probe.

SELDI also has been called "affinity capture mass spectrometry" or "Surface-Enhanced Affinity Capture" ("SEAC"). This version involves the use of probes that have a material on the probe surface that captures analytes through a non-covalent affinity interaction (adsorption) between the material and the analyte. The material is variously called an "adsorbent," a "capture reagent," an "affinity reagent" or a "binding moiety." Such probes can be referred to as "affinity capture probes" and as having an "adsorbent surface." The capture reagent can be any material capable of binding an analyte. The capture reagent is attached to the probe surface by physisorption or chemisorption. In certain embodiments the probes have the capture reagent already attached to the surface. In other embodiments, the probes are pre-activated and include a reactive moiety that is capable of binding the capture reagent, e.g., through a reaction forming a covalent or coordinate covalent bond. Epoxide and acyl-imidizole are useful reactive moieties to covalently bind polypeptide capture reagents such as antibodies or cellular receptors. Nitrilotriacetic acid and iminodiacetic acid are useful reactive moieties that function as chelating agents to bind metal ions that interact non-covalently with histidine containing peptides. Adsorbents are generally classified as chromatographic adsorbents and biospecific adsorbents.

"Chromatographic adsorbent" refers to an adsorbent material typically used in chromatography. Chromatographic adsorbents include, for example, ion exchange materials, metal chelators (e.g., nitrilotriacetic acid or iminodiacetic acid), immobilized metal chelates, hydrophobic interaction adsorbents, hydrophilic interaction adsorbents, dyes, simple biomolecules (e.g., nucleotides, amino acids, simple sugars and fatty acids) and mixed mode adsorbents (e.g., hydrophobic attraction/electrostatic repulsion adsorbents).

"Biospecific adsorbent" refers to an adsorbent comprising a biomolecule, e.g., a nucleic acid molecule (e.g., an aptamer), a polypeptide, a polysaccharide, a lipid, a steroid or a conjugate of these (e.g., a glycoprotein, a lipoprotein, a glycolipid, a nucleic acid (e.g., DNA)-protein conjugate). In certain instances, the biospecific adsorbent can be a macromolecular structure such as a multiprotein complex, a biological membrane or a virus. Examples of biospecific adsorbents are antibodies, receptor proteins and nucleic acids. Biospecific adsorbents typically have higher specificity for a target analyte than chromatographic adsorbents. Further examples of adsorbents for use in SELDI can be found in U.S. Pat. No. 6,225,047. A "bioselective adsorbent" refers to an adsorbent that binds to an analyte with an affinity of at least $10^{-8}$ M.

Protein biochips produced by Ciphergen Biosystems, Inc. comprise surfaces having chromatographic or biospecific adsorbents attached thereto at addressable locations. Ciphergen's ProteinChip® arrays include NP20 (hydrophilic); H4 and H50 (hydrophobic); SAX-2, Q-10 and LSAX-30 (anion exchange); WCX-2, and CM-10 and LWCX-30 (cation exchange); IMAC-3, IMAC-30 and IMAC-50 (metal chelate); and PS-10, PS-20 (reactive surface with acyl-imidizole, epoxide) and PG-20 (protein G coupled through acyl-imidizole). Hydrophobic ProteinChip arrays have isopropyl or nonylphenoxy-poly(ethylene glycol)methacrylate functionalities. Anion exchange ProteinChip arrays have quaternary ammonium functionalities. Cation exchange ProteinChip arrays have carboxylate functionalities. Immobilized metal chelate ProteinChip arrays have nitrilotriacetic acid functionalities (IMAC 3 and IMAC 30) or O-methacryloyl-N,N-bis-carboxymethyl tyrosine funtionalities (IMAC 50) that adsorb transition metal ions, such as copper, nickel, zinc, and gallium, by chelation. Preactivated ProteinChip arrays have acyl-imidizole or epoxide functional groups that can react with groups on proteins for covalent binding.

Such biochips are further described in: U.S. Pat. No. 6,579,719 (Hutchens and Yip, "Retentate Chromatography," Jun. 17, 2003); U.S. Pat. No. 6,897,072 (Rich et al., "Probes for a Gas Phase Ion Spectrometer," May 24, 2005); U.S. Pat. No. 6,555,813 (Beecher et al., "Sample Holder with Hydrophobic Coating for Gas Phase Mass Spectrometer," Apr. 29, 2003); U.S. Patent Publication No. U.S. 2003-0032043 A1 (Pohl and Papanu, "Latex Based Adsorbent Chip," Jul. 16, 2002); and PCT International Publication No. WO 03/040700 (Um et al., "Hydrophobic Surface Chip," May 15, 2003); U.S. Patent Publication No. US 2003-0218130 A1 (Boschetti et al., "Biochips With Surfaces Coated With Polysaccharide-Based Hydrogels," Apr. 14, 2003) and U.S. Pat. No. 7,045,366 (Huang et al., "Photocrosslinked Hydrogel Blend Surface Coatings," May 16, 2006).

In general, a probe with an adsorbent surface is contacted with the sample for a period of time sufficient to allow the biomarker or biomarkers that may be present in the sample to bind to the adsorbent. After an incubation period, the substrate is washed to remove unbound material. Any suitable washing solutions can be used; preferably, aqueous solutions are employed. The extent to which molecules remain bound can be manipulated by adjusting the stringency of the wash. The elution characteristics of a wash solution can depend, for example, on pH, ionic strength, hydrophobicity, degree of chaotropism, detergent strength, and temperature. Unless the probe has both SEAC and SEND properties (as described herein), an energy absorbing molecule then is applied to the substrate with the bound biomarkers.

In yet another method, one can capture the biomarkers with a solid-phase bound immuno-adsorbent that has antibodies that bind the biomarkers. After washing the adsorbent to remove unbound material, the biomarkers are eluted from the solid phase and detected by applying to a SELDI biochip that binds the biomarkers and analyzing by SELDI.

The biomarkers bound to the substrates are detected in a gas phase ion spectrometer such as a time-of-flight mass spectrometer. The biomarkers are ionized by an ionization source such as a laser, the generated ions are collected by an ion optic assembly, and then a mass analyzer disperses and analyzes the passing ions. The detector then translates information of the detected ions into mass-to-charge ratios. Detection of a biomarker typically will involve detection of signal intensity. Thus, both the quantity and mass of the biomarker can be determined.

SEND

Another method of laser desorption mass spectrometry is called Surface-Enhanced Neat Desorption ("SEND"). SEND involves the use of probes comprising energy absorbing molecules that are chemically bound to the probe surface ("SEND probe"). The phrase "energy absorbing molecules" (EAM) denotes molecules that are capable of absorbing energy from a laser desorption/ionization source and, thereafter, contribute to desorption and ionization of analyte molecules in contact therewith. The EAM category includes molecules used in MALDI, frequently referred to as "matrix," and is exemplified by cinnamic acid derivatives, sinapinic acid (SPA), cyano-hydroxy-cinnamic acid (CHCA) and dihydroxybenzoic acid, ferulic acid, and hydroxyaceto-phenone derivatives. In certain embodiments, the energy absorbing molecule is incorporated into a linear or cross-linked polymer, e.g., a polymethacrylate. For example, the composition can be a co-polymer of α-cyano-4-methacryloyloxycinnamic acid and acrylate. In another embodiment, the composition is a co-polymer of α-cyano-4-methacryloyloxycinnamic acid, acrylate and 3-(tri-ethoxy)silyl propyl methacrylate. In another embodiment, the composition is a co-polymer of α-cyano-4-methacryloyloxycinnamic acid and octadecyl-methacrylate ("C18 SEND"). SEND is further described in U.S. Pat. No. 6,124,137 and PCT International Publication No. WO 03/64594 (Kitagawa, "Monomers And Polymers Having Energy Absorbing Moieties Of Use In Desorption/Ionization Of Analytes," Aug. 7, 2003).

SEAC/SEND is a version of SELDI laser desorption mass spectrometry in which both a capture reagent and an energy absorbing molecule are attached to the sample presenting surface. SEAC/SEND probes therefore allow the capture of analytes through affinity capture and ionization/desorption without the need to apply external matrix. The C18 SEND biochip is a version of SEAC/SEND, comprising a C18 moiety which functions as a capture reagent, and a CHCA moiety which functions as an energy absorbing moiety.

SEPAR

Another version of LDI is called Surface-Enhanced Photolabile Attachment and Release ("SEPAR"). SEPAR involves the use of probes having moieties attached to the surface that can covalently bind an analyte, and then release the analyte through breaking a photolabile bond in the moiety after exposure to light, e.g., to laser light (see, U.S. Pat. No. 5,719,060). SEPAR and other forms of SELDI are readily adapted to detecting a biomarker or biomarker profile, pursuant to the present invention.

MALDI

MALDI is a traditional method of laser desorption/ionization used to analyte biomolecules such as proteins and nucleic acids. In one MALDI method, the sample is mixed with matrix and deposited directly on a MALDI array. However, the complexity of biological samples such as serum and urine makes this method less than optimal without prior fractionation of the sample. Accordingly, in certain embodiments with biomarkers are preferably first captured with biospecific (e.g., an antibody) or chromatographic materials coupled to a solid support such as a resin (e.g., in a spin column). Specific affinity materials that bind the biomarkers of this invention are described above. After purification on the affinity material, the biomarkers are eluted and then detected by MALDI.

In another mass spectrometry method, the biomarkers can be first captured on a chromatographic resin having chromatographic properties that bind the biomarkers. In the present example, this could include a variety of methods. For example, one could capture the biomarkers on a cation exchange resin, such as CM Ceramic HyperD F resin, wash the resin, elute the biomarkers and detect by MALDI. Alternatively, this method could be preceded by fractionating the sample on an anion exchange resin before application to the cation exchange resin. In another alternative, one could fractionate on an anion exchange resin and detect by MALDI directly. In yet another method, one could capture the biomarkers on an immuno-chromatographic resin that comprises antibodies that bind the biomarkers, wash the resin to remove unbound material, elute the biomarkers from the resin and detect the eluted biomarkers by MALDI or by SELDI.

Other Forms of Ionization in Mass Spectrometry

In another method, the biomarkers are detected by LC-MS or LC-LC-MS. This involves resolving the proteins in a sample by one or two passes through liquid chromatography, followed by mass spectrometry analysis, typically electrospray ionization.

Data Analysis

Analysis of analytes by time-of-flight mass spectrometry generates a time-of-flight spectrum. The time-of-flight spectrum ultimately analyzed typically does not represent the signal from a single pulse of ionizing energy against a sample, but rather the sum of signals from a number of pulses. This reduces noise and increases dynamic range. This time-of-flight data is then subject to data processing. In Ciphergen's ProteinChip® software, data processing typically includes TOF-to-M/Z transformation to generate a mass spectrum, baseline subtraction to eliminate instrument offsets and high frequency noise filtering to reduce high frequency noise.

Data generated by desorption and detection of biomarkers can be analyzed with the use of a programmable digital computer. The computer program analyzes the data to indicate the number of biomarkers detected, and optionally the strength of the signal and the determined molecular mass for each biomarker detected. Data analysis can include steps of determining signal strength of a biomarker and removing data deviating from a predetermined statistical distribution. For example, the observed peaks can be normalized, by calculating the height of each peak relative to some reference. The reference can be background noise generated by the instrument and chemicals such as the energy absorbing molecule which is set at zero in the scale.

The computer can transform the resulting data into various formats for display. The standard spectrum can be displayed, but in one useful format only the peak height and mass information are retained from the spectrum view, yielding a cleaner image and enabling biomarkers with nearly identical molecular weights to be more easily seen. In another useful format, two or more spectra are compared, conveniently highlighting unique biomarkers and biomarkers that are up- or down-regulated between samples. Using any of these formats, one can readily determine whether a particular biomarker is present in a sample.

Analysis generally involves the identification of peaks in the spectrum that represent signal from an analyte. Peak selection can be done visually, but software is available, as part of Ciphergen's ProteinChip® software package, that can automate the detection of peaks. In general, this software functions by identifying signals having a signal-to-noise ratio above a selected threshold and labeling the mass of the peak at the centroid of the peak signal. In one useful application, many spectra are compared to identify identical peaks present in some selected percentage of the mass spectra. One version of this software clusters all peaks appearing in the various spectra within a defined mass range, and assigns a mass (M/Z) to all the peaks that are near the mid-point of the mass (M/Z) cluster.

Software used to analyze the data can include code that applies an algorithm to the analysis of the signal to determine whether the signal represents a peak in a signal that corresponds to a biomarker according to the present invention. The software also can subject the data regarding observed biomarker peaks to classification tree or ANN analysis, to determine whether a biomarker peak or combination of biomarker peaks is present that indicates the status of the particular clinical parameter under examination. Analysis of the data may be "keyed" to a variety of parameters that are obtained, either directly or indirectly, from the mass spectrometric analysis of the sample. These parameters include, but are not limited to, the presence or absence of one or more peaks, the shape of a peak or group of peaks, the height of one or more peaks, the log of the height of one or more peaks, and other arithmetic manipulations of peak height data.

General Protocol for SELDI Detection of Biomarkers for Alzheimer's Disease

A preferred protocol for the detection of the biomarkers of this invention is as follows. The sample to be tested is then contacted with an affinity capture probe comprising an anion exchange adsorbent, e.g., a Q10 ProteinChip, as indicated in Table 1. The probe is washed with a buffer that will retain the biomarker while washing away unbound molecules. A suitable wash for the VGF peptide biomarker when binding to a Q10 ProteinChip is a 100 mM Tris buffer at pH 9. The biomarkers are detected by laser desorption/ionization mass spectrometry.

Alternatively, if antibodies that recognize the biomarker are available, these can be attached to the surface of a probe, such as a pre-activated PS10 or PS20 ProteinChip array (Ciphergen Biosystems, Inc.). These antibodies can capture the biomarkers from a sample onto the probe surface. Then the biomarkers can be detected by, e.g., laser desorption/ionization mass spectrometry.

Detection by Immunoassay

In another embodiment of the invention, the biomarkers of the invention are measured by a method other than mass spectrometry or other than methods that rely on a measurement of the mass of the biomarker. In one such embodiment that does not rely on mass, the biomarkers of this invention can be measured by immunoassay. Immunoassay requires biospecific capture reagents, such as antibodies, to capture the biomarkers. Antibodies can be produced by methods well known in the art, e.g., by immunizing animals with the biomarkers. Biomarkers can be isolated from samples based on their binding characteristics. Alternatively, if the amino acid sequence of a polypeptide biomarker is known, the polypeptide can be synthesized and used to generate antibodies by methods well known in the art.

This invention contemplates traditional immunoassays including, for example, sandwich immunoassays including ELISA or fluorescence-based immunoassays, as well as other enzyme immunoassays. In the SELDI-based immunoassay, a biospecific capture reagent for the biomarker is attached to the surface of an MS probe, such as a pre-activated ProteinChip array. The biomarker is then specifically captured on the biochip through this reagent, and the captured biomarker is detected by mass spectrometry.

V. Determination of Subject Alzheimer's Disease Status

The biomarkers of the invention can be used in diagnostic tests to assess Alzheimer's disease status in a subject, e.g., to diagnose Alzheimer's disease. The phrase "Alzheimer's disease status" includes any distinguishable manifestation of the disease, including non-Alzheimer's disease, e.g., normal or non-demented. For example, disease status includes, without limitation, the presence or absence of Alzheimer's disease (e.g., Alzheimer's disease v. non-Alzheimer's disease), the risk of developing disease, the stage of the disease, the progress of disease (e.g., progress of disease or remission of disease over time) and the effectiveness or response to treatment of disease. Based on this status, further procedures may be indicated, including additional diagnostic tests or therapeutic procedures or regimens.

The power of a diagnostic test to correctly predict status is commonly measured as the sensitivity of the assay, the specificity of the assay or the area under a receiver operated characteristic ("ROC") curve. Sensitivity is the percentage of true positives that are predicted by a test to be positive, while specificity is the percentage of true negatives that are predicted by a test to be negative. An ROC curve provides the sensitivity of a test as a function of 1-specificity. The greater the area under the ROC curve, the more powerful the predictive value of the test. Other useful measures of the utility of a test are positive predictive value and negative predictive value. Positive predictive value is the percentage of people who test positive that is actually positive. Negative predictive value is the percentage of people who test negative that is actually negative.

The biomarkers of this invention show a statistical difference in different Alzheimer's disease statuses of at least $p \leq 0.05$, $p \leq 10^{-2}$, $p \leq 10^{-3}$, $p \leq 10^{-4}$ or $p \leq 10^{-5}$. Diagnostic tests that use these biomarkers alone or in combination show a sensitivity and specificity of at least 75%, at least 80%, at least 85%, at least 90%, at least 95%, at least 98% and about 100%.

Single Markers

VGF peptide-1 is differentially present in Alzheimer's disease, and, therefore, is individually useful in aiding in the determination of Alzheimer's disease status. The method involves, first, measuring the VGF peptide in a subject sample using the methods described herein, e.g., capture on a SELDI biochip followed by detection by mass spectrometry and, second, comparing the measurement with a diagnostic amount or cut-off that distinguishes a positive Alzheimer's disease status from a negative Alzheimer's disease status. The diagnostic amount represents a measured amount of a biomarker above which or below which a subject is classified as having a particular Alzheimer's disease status. For example, VGF peptide is up-regulated compared to normal during Alzheimer's disease. Therefore, a measured amount above the diagnostic cutoff provides a diagnosis of Alzheimer's disease. As is well understood in the art, by adjusting the particular diagnostic cut-off used in an assay, one can increase sensitivity or specificity of the diagnostic assay depending on the preference of the diagnostician. The particular diagnostic cut-off can be determined, for example, by measuring the amount of the biomarker in a statistically significant number of samples from subjects with the different Alzheimer's disease statuses, as was done here, and drawing the cut-off to suit the diagnostician's desired levels of specificity and sensitivity.

Combinations of Markers

While individual biomarkers are useful diagnostic biomarkers, it has been found that a combination of biomarkers can provide greater predictive value of a particular status than single biomarkers alone. Specifically, the detection of a plurality of biomarkers in a sample can increase the sensitivity and/or specificity of the test. A combination of at least two biomarkers is sometimes referred to as a "biomarker profile" or "biomarker fingerprint."

Alzheimer's Disease Status

Determining Alzheimer's disease status typically involves classifying an individual into one of two or more groups (statuses) based on the results of the diagnostic test. The diagnostic tests described herein can be used to classify between a number of different states.

Determining Presence of Disease

In one embodiment, this invention provides methods for determining the presence or absence of Alzheimer's disease in a subject (status: Alzheimer's disease v. non-Alzheimer's disease). The presence or absence of Alzheimer's disease is determined by measuring the relevant biomarker or biomarkers and then either submitting them to a classification algorithm or comparing them with a reference amount and/or pattern of biomarkers that is associated with the particular risk level.

Determining Risk of Developing Disease

In one embodiment, this invention provides methods for determining the risk of developing disease in a subject. Biomarker amounts or patterns are characteristic of various risk states, e.g., high, medium or low. The risk of developing a disease is determined by measuring the relevant biomarker or biomarkers and then either submitting them to a classification algorithm or comparing them with a reference amount and/or pattern of biomarkers that is associated with the particular risk level.

Determining Stage of Disease

In one embodiment, this invention provides methods for determining the stage of disease in a subject. Each stage of the disease has a characteristic amount of a biomarker or relative amounts of a set of biomarkers (a pattern). The stage of a disease is determined by measuring the relevant biomarker or biomarkers and then either submitting them to a classification algorithm or comparing them with a reference amount and/or pattern of biomarkers that is associated with the particular stage.

Determining Course (Progression/Remission) of Disease

In one embodiment, this invention provides methods for determining the course of disease in a subject. Disease course refers to changes in disease status over time, including disease progression (worsening) and disease regression (improvement). Over time, the amounts or relative amounts (e.g., the pattern) of the biomarkers changes. For example, the VGF peptide biomarker in Table 1 increases with disease. Therefore, increasing amounts of this biomarker indicates the course of the disease. Accordingly, this method involves measuring one or more biomarkers in a subject at two or more different time points, e.g., a first time and a second time, and comparing the change in amounts, if any. The course of disease is determined based on these comparisons.

Similarly, changes in the rate of disease progression (or regression) may be monitored by measuring the amount of a biomarker, e.g., the VGF peptide biomarker of Table 1, at different times and calculating the rate of change in biomarker levels. The ability to measure disease state or velocity of disease progression can be important for drug treatment studies where the goal is to slow down or arrest disease progression through therapy.

Reporting the Status

Similarly, changes in the rate of disease progression (or regression) may be monitored by measuring the amount of a biomarker, e.g., the VGF peptide biomarker of Table 1, at different times and calculating the rate of change in biomarker levels. The ability to measure disease state or velocity of disease progression can be important for drug treatment studies where the goal is to slow down or arrest disease progression through therapy.

Additional embodiments of the invention relate to the communication of assay results or diagnoses or both to technicians, physicians or patients, for example. In certain embodiments, computers will be used to communicate assay results or diagnoses or both to interested parties, e.g., physicians and their patients. In some embodiments, the assays will be performed or the assay results analyzed in a country or jurisdiction which differs from the country or jurisdiction to which the results or diagnoses are communicated.

In a preferred embodiment of the invention, a diagnosis based on the differential presence in a test subject of any the VGF peptide biomarkers is communicated to the subject as soon as possible after the diagnosis is obtained. The diagnosis may be communicated to the subject by the subject's treating physician. Alternatively, the diagnosis may be sent to a test subject by email or communicated to the subject by phone. A computer may be used to communicate the diagnosis by email or phone. In certain embodiments, the message containing results of a diagnostic test may be generated and delivered automatically to the subject using a combination of computer hardware and software which will be familiar to artisans skilled in telecommunications. One example of a healthcare-oriented communications system is described in U.S. Pat. No. 6,283,761; however, the present invention is not limited to methods which utilize this particular communications system. In certain embodiments of the methods of the invention, all or some of the method steps, including the assaying of samples, diagnosing of diseases, and communicating of assay results or diagnoses, may be carried out in diverse (e.g., foreign) jurisdictions.

Subject Management

In certain embodiments of the methods of qualifying Alzheimer's disease status, the methods further comprise managing subject treatment based on the status. Such management includes the actions of the physician or clinician subsequent to determining Alzheimer's disease status. For example, if a physician makes a diagnosis of Alzheimer's disease, then a certain regime of treatment, such as prescription or administration of a cholinesterase inhibitor might follow. Alternatively, a diagnosis of non-Alzheimer's disease or non-Alzheimer's disease might be followed with further testing to determine a specific disease that might the patient might be suffering from. Also, if the diagnostic test gives an inconclusive result on Alzheimer's disease status, further tests may be called for.

Additional embodiments of the invention relate to the communication of assay results or diagnoses or both to technicians, physicians or patients, for example. In certain embodiments, computers will be used to communicate assay results or diagnoses or both to interested parties, e.g., physicians and their patients. In some embodiments, the assays will be performed or the assay results analyzed in a country or jurisdiction which differs from the country or jurisdiction to which the results or diagnoses are communicated.

In a preferred embodiment of the invention, a diagnosis based on the presence or absence in a test subject of the VGF peptide of Table 1 is communicated to the subject as soon as possible after the diagnosis is obtained. The diagnosis may be communicated to the subject by the subject's treating physician. Alternatively, the diagnosis may be sent to a test subject by email or communicated to the subject by phone. A computer may be used to communicate the diagnosis by email or phone. In certain embodiments, the message containing results of a diagnostic test may be generated and delivered automatically to the subject using a combination of computer hardware and software which will be familiar to artisans skilled in telecommunications. One example of a healthcare-oriented communications system is described in U.S. Pat. No. 6,283,761; however, the present invention is not limited to methods which utilize this particular communications system. In certain embodiments of the methods of the invention, all or some of the method steps, including the assaying of samples, diagnosing of diseases, and communicating of assay results or diagnoses, may be carried out in diverse (e.g., foreign) jurisdictions.

VI. Determining Therapeutic Efficacy of Pharmaceutical Drug

In another embodiment, this invention provides methods for determining the therapeutic efficacy of a pharmaceutical drug. These methods are useful in performing clinical trials of the drug, as well as monitoring the progress of a patient on the drug. Therapy or clinical trials involve administering the drug in a particular regimen. The regimen may involve a single dose of the drug or multiple doses of the drug over time. The doctor or clinical researcher monitors the effect of the drug on the patient or subject over the course of administration. If the drug has a pharmacological impact on the condition, the amounts or relative amounts (e.g., the pattern or profile) of the biomarkers of this invention changes toward a non-disease profile. For example, VGF peptide biomarker is increased in disease. Therefore, one can follow the course of the amounts of these biomarkers in the subject during the course of treatment. Accordingly, this method involves measuring one or more biomarkers in a subject receiving drug therapy, and correlating the amounts of the biomarkers with the disease status of the subject. One embodiment of this method involves determining the levels of the biomarkers at at least two different time points during a course of drug therapy, e.g., a first time and a second time, and comparing the change in amounts of the biomarkers, if any. For example, the biomarkers can be measured before and after drug administration or at two different time points during drug administration. The effect of therapy is determined based on these comparisons. If a treatment is effective, then the biomarkers will trend toward normal, while if treatment is ineffective, the biomarkers will trend toward disease indications. If a treatment is effective, then the biomarkers will trend toward normal, while if treatment is ineffective, the biomarkers will trend toward disease indications.

VII. Generation of Classification Algorithms for Qualifying Alzheimer'S Disease Status In some embodiments, data derived from the spectra (e.g., mass spectra or time-of-flight spectra) that are generated using samples such as "known samples" can then be used to "train" a classification model. A "known sample" is a sample that has been pre-classified. The data that are derived from the spectra and are used to form the classification model can be referred to as a "training data set." Once trained, the classification model can recognize patterns in data derived from spectra generated using unknown samples. The classification model can then be used to classify the unknown samples into classes. This can be useful, for example, in predicting whether or not a particular biological sample is associated with a certain biological condition (e.g., diseased versus non-diseased).

The training data set that is used to form the classification model may comprise raw data or pre-processed data. In some embodiments, raw data can be obtained directly from time-of-flight spectra or mass spectra, and then may be optionally "pre-processed" as described above.

Classification models can be formed using any suitable statistical classification (or "learning") method that attempts to segregate bodies of data into classes based on objective parameters present in the data. Classification methods may be either supervised or unsupervised. Examples of supervised and unsupervised classification processes are described in Jain, "Statistical Pattern Recognition: A Review", *IEEE Transactions on Pattern Analysis and Machine Intelligence*, Vol. 22, No. 1, January 2000, the teachings of which are incorporated by reference.

In supervised classification, training data containing examples of known categories are presented to a learning mechanism, which learns one or more sets of relationships that define each of the known classes. New data may then be applied to the learning mechanism, which then classifies the new data using the learned relationships. Examples of supervised classification processes include linear regression processes (e.g., multiple linear regression (MLR), partial least squares (PLS) regression and principal components regression (PCR)), binary decision trees (e.g., recursive partitioning processes such as CART—classification and regression trees), artificial neural networks such as back propagation networks, discriminant analyses (e.g., Bayesian classifier or Fischer analysis), logistic classifiers, and support vector classifiers (support vector machines).

A preferred supervised classification method is a recursive partitioning process. Recursive partitioning processes use recursive partitioning trees to classify spectra derived from unknown samples. Further details about recursive partitioning processes are provided in U.S. Patent Application No. 2002 0138208 A1 to Paulse et al., "Method for analyzing mass spectra."

In other embodiments, the classification models that are created can be formed using unsupervised learning methods. Unsupervised classification attempts to learn classifications based on similarities in the training data set, without pre-classifying the spectra from which the training data set was derived. Unsupervised learning methods include cluster analyses. A cluster analysis attempts to divide the data into "clusters" or groups that ideally should have members that are very similar to each other, and very dissimilar to members of other clusters. Similarity is then measured using some distance metric, which measures the distance between data items, and clusters together data items that are closer to each other. Clustering techniques include the MacQueen's K-means algorithm and the Kohonen's Self-Organizing Map algorithm.

Learning algorithms asserted for use in classifying biological information are described, for example, in PCT International Publication No. WO 01/31580 (Barnhill et al., "Methods and devices for identifying patterns in biological systems and methods of use thereof"), U.S. Patent Application No. 2002 0193950 A1 (Gavin et al., "Method or analyzing mass spectra"), U.S. Patent Application No. 2003 0004402 A1 (Hitt et al., "Process for discriminating between biological states based on hidden patterns from biological data"), and U.S. Patent Application No. 2003 0055615 A1 (Zhang and Zhang, "Systems and methods for processing biological expression data").

The classification models can be formed on and used on any suitable digital computer. Suitable digital computers include micro, mini, or large computers using any standard or specialized operating system, such as a Unix, Windows™ or Linux™ based operating system. The digital computer that is used may be physically separate from the mass spectrometer that is used to create the spectra of interest, or it may be coupled to the mass spectrometer.

The training data set and the classification models according to embodiments of the invention can be embodied by computer code that is executed or used by a digital computer. The computer code can be stored on any suitable computer readable media including optical or magnetic disks, sticks, tapes, etc., and can be written in any suitable computer programming language including C, C++, visual basic, etc.

The learning algorithms described above are useful both for developing classification algorithms for the biomarkers already discovered, or for finding new biomarkers for Alzheimer's disease. The classification algorithms, in turn, form the base for diagnostic tests by providing diagnostic values (e.g., cut-off points) for biomarkers used singly or in combination.

VIII. Use of Biomarkers for Imaging

Non-invasive medical imaging techniques such as Positron Emisson Tomography (PET) or single photon emission computerized tomography (SPECT) imaging are particularly useful for the detection of cancer, coronary artery disease and brain disease. PET and SPECT imaging shows the chemical functioning of organs and tissues, while other imaging techniques—such as X-ray, CT and MRI—show structure. The use of PET and SPECT imaging has become increasingly useful for qualifying and monitoring the development of brain diseases such as Alzheimer's disease. In some instances, the use of PET or SPECT imaging allows Alzheimer's disease to be detected several years earlier than the onset of symptoms. See, e.g., Vassaux and Groot-wassink, "In Vivo Noninvasive Imaging for Gene Therapy," J. Biomedicine and Biotechnology, 2: 92-101 (2003).

Different strategies are being used to develop compounds suitable for in vivo imaging of amyloid deposits in human brains. Monoclonal antibodies against A-beta and peptide fragments have had limited uptake by the brain when tested in patients with AD. The small molecular approach for amyloid imaging has so far been most successful, as described by, e.g., Nordberg A, Lancet Neurol., 3(9):519-27 (2004); Kung M P et al, Brain Res., 1025(1-2):98-105 (2004); Herholz K et al., Mol Imaging Biol., 6(4):239-69 (2004); Neuropsychol Rev., Zakzanis K K et al., 13(1):1-18 (2003); Herholz K, Ann Nucl Med., 17(2):79-89 (2003).

The peptide biomarkers disclosed herein, or fragments thereof, can be used in the context of PET and SPECT imaging applications. After modification with appropriate tracer residues for PET or SPECT applications, peptide biomarkers which interact with amyloid plaque proteins can be used to image the deposition of amyloid plaques in Alzheimer's patients.

Antisense technology may be used to detect expression of transcripts whose translation is correlated with the biomarkers identified herein. For example, the use of antisense peptide nucleic acid (PNA) labeled with an appropriate radionuclide, such as $^{111}$In, and conjugated to a brain drug-targeting system to enable transport across biologic membrane barriers, has been demonstrated to allow imaging of endogenous gene expression in brain cancer. See Suzuki et al., Journal of Nuclear Medicine, 10: 1766-1775 (2004). Suzuki et al. utilize a delivery system comprising monoclonal antibodies that target transferring receptors at the blood-brain barrier and facilitate transport of the PNA across that barrier.

IX. Compositions of Matter

In another aspect, this invention provides compositions of matter based on the biomarkers of this invention.

In one embodiment, this invention provides biomarkers of this invention in purified form. Purified biomarkers have utility as antigens to raise antibodies. Purified biomarkers also have utility as standards in assay procedures. As used herein, a "purified biomarker" is a biomarker that has been isolated from other proteins and peptdies, and/or other material from the biological sample in which the biomarker is found. Biomarkers may be purified using any method known in the art, including, but not limited to, mechanical separation (e.g., centrifugation), ammonium sulphate precipitation, dialysis (including size-exclusion dialysis), size-exclusion chromatography, affinity chromatography, anion-exchange chromatography, cation-exchange chromatography, and metal-chelate chromatography. Such methods may be performed at any appropriate scale, for example, in a chromatography column, or on a biochip.

In another embodiment, this invention provides biospecific capture reagents that specifically bind a biomarker of this invention, optionally in purified form. Preferably, a biospecific capture reagent is an antibody. In one embodiment, a biospecific capture reagent is an antibody that binds a biomarker of this invention.

In another embodiment, this invention provides a complex between a biomarker of this invention and biospecific capture reagent that specifically binds the biomarker. In other embodiments, the biospecific capture reagent is bound to a solid phase. For example, this invention contemplates a device comprising bead or chip derivatized with a biospecific capture reagent that binds to a biomarker of this invention and, also, the device in which a biomarker of this invention is bound to the biospecific capture reagent.

In another embodiment, this invention provides a device comprising a solid substrate to which is attached an adsorbent, e.g., a chromatographic adsorbent, to which is further bound a biomarker of this invention.

X. Kits for Detection of Biomarkers for Alzheimer's Disease

In another aspect, the present invention provides kits for qualifying Alzheimer's disease status, which kits are used to detect biomarkers according to the invention. In one embodiment, the kit comprises a solid support, such as a chip, a microtiter plate or a bead or resin having a capture reagent attached thereon, wherein the capture reagent binds a biomarker of the invention. Thus, for example, the kits of the present invention can comprise mass spectrometry probes for SELDI, such as ProteinChip® arrays. In the case of biospecfic capture reagents, the kit can comprise a solid support with a reactive surface, and a container comprising the biospecific capture reagent.

The kit can also comprise a washing solution or instructions for making a washing solution, in which the combination of the capture reagent and the washing solution allows capture of the biomarker or biomarkers on the solid support for subsequent detection by, e.g., mass spectrometry. The kit may include more than type of adsorbent, each present on a different solid support.

In a further embodiment, such a kit can comprise instructions for suitable operational parameters in the form of a label or separate insert. For example, the instructions may inform a consumer about how to collect the sample, how to wash the probe or the particular biomarkers to be detected.

In yet another embodiment, the kit can comprise one or more containers with biomarker samples, to be used as standard(s) for calibration.

XI. Use of Biomarkers for Alzheimer's Disease in Screening Assays and Methods of Treating Alzheimer's Disease The methods of the present invention have other applications as well. For example, the biomarkers can be used to screen for compounds that modulate the expression of the biomarkers in vitro or in vivo, which compounds in turn may be useful in treating or preventing Alzheimer's disease in patients. In another example, the biomarkers can be used to monitor the response to treatments for Alzheimer's disease. In yet another example, the biomarkers can be used in heredity studies to determine if the subject is at risk for developing Alzheimer's disease.

Thus, for example, the kits of this invention could include a solid substrate having a hydrophobic function, such as a protein biochip (e.g., a Ciphergen Q10 ProteinChip array, e.g., ProteinChip array) and a sodium acetate buffer for washing the substrate, as well as instructions providing a protocol to measure the biomarkers of this invention on the chip and to use these measurements to diagnose Alzheimer's disease.

Compounds suitable for therapeutic testing may be screened initially by identifying compounds which interact with one or more biomarkers listed in Table I. By way of example, screening might include recombinantly expressing a biomarker listed in Table I, purifying the biomarker, and affixing the biomarker to a substrate. Test compounds would then be contacted with the substrate, typically in aqueous conditions, and interactions between the test compound and the biomarker are measured, for example, by measuring elution rates as a function of salt concentration. Certain proteins may recognize and cleave one or more biomarkers of Table I, in which case the proteins may be detected by monitoring the digestion of one or more biomarkers in a standard assay, e.g., by gel electrophoresis of the proteins.

In a related embodiment, the ability of a test compound to inhibit the activity of VGF peptide may be measured. One skilled in the art will recognize that the techniques used to measure the activity of a particular biomarker will vary depending on the function and properties of the biomarker. For example, an enzymatic activity of a biomarker may be assayed provided that an appropriate substrate is available and provided that the concentration of the substrate or the appearance of the reaction product is readily measurable. The ability of potentially therapeutic test compounds to inhibit or enhance the activity of a given biomarker may be determined by measuring the rates of catalysis in the presence or absence of the test compounds. The ability of a test compound to interfere with a non-enzymatic (e.g., structural) function or activity of one of the biomarkers of Table I may also be measured. For example, the self-assembly of a multi-protein complex which includes the VGF peptide may be monitored by spectroscopy in the presence or absence of a test compound. Alternatively, if the biomarker is a non-enzymatic enhancer of transcription, test compounds which interfere with the ability of the biomarker to enhance transcription may be identified by measuring the levels of biomarker-dependent transcription in vivo or in vitro in the presence and absence of the test compound.

Test compounds capable of modulating the activity of the VGF peptide may be administered to patients who are suffering from or are at risk of developing Alzheimer's disease or other cancer. For example, the administration of a test compound which increases the activity of a particular biomarker may decrease the risk of Alzheimer's disease in a patient if the activity of the particular biomarker in vivo prevents the accumulation of proteins for Alzheimer's disease. Conversely, the administration of a test compound which decreases the activity of a particular biomarker may decrease the risk of Alzheimer's disease in a patient if the increased activity of the biomarker is responsible, at least in part, for the onset of Alzheimer's disease.

In an additional aspect, the invention provides a method for identifying compounds useful for the treatment of disorders such as Alzheimer's disease which are associated with increased levels of modified forms of a native protein. For example, in one embodiment, cell extracts or expression libraries may be screened for compounds which catalyze the cleavage of full-length VGF protein to form the VGF peptide of Table 1. In one embodiment of such a screening assay, cleavage of native VGF protein or the VGF peptide may be detected by attaching a fluorophore to the protein which remains quenched when protein is uncleaved but which fluoresces when the protein is cleaved. Alternatively, a modified version of VGF where the amide bond between the amino acids at the N- and C-terminus of the VGF peptide uncleavable may be used to selectively bind or "trap" the cellular proteases which cleaves full-length VGF protein at that site in vivo. Methods for screening and identifying proteases and their targets are well-documented in the scientific literature, e.g., in Lopez-Ottin et al. (Nature Reviews, 3:509-519 (2002)).

At the clinical level, screening a test compound for use in treating Alzheimer's disease includes obtaining samples from test subjects before and after the subjects have been exposed to a test compound. The levels in the samples of the VGF peptide of Table 1 may be measured and analyzed to determine whether the levels of the biomarkers change after exposure to a test compound. The samples may be analyzed by mass spectrometry, as described herein, or the samples may be analyzed by any appropriate means known to one of skill in the art. For example, the levels of one or more of the biomarkers listed in Table I may be measured directly by Western blot using radio- or fluorescently-labeled antibodies which specifically bind to the biomarkers. Alternatively, changes in the levels of mRNA encoding the one or more biomarkers may be measured and correlated with the administration of a given test compound to a subject. In a further embodiment, the changes in the level of expression of one or more of the biomarkers may be measured using in vitro methods and materials. For example, human tissue cultured cells which express, or are capable of expressing, one or more of the biomarkers of Table I may be contacted with test compounds. Subjects who have been treated with test compounds will be routinely examined for any physiological effects which may result from the treatment. In particular, the test compounds will be evaluated for their ability to decrease disease likelihood in a subject. Alternatively, if the test compounds are administered to subjects who have previously been diagnosed with Alzheimer's disease, test compounds will be screened for their ability to slow or stop the progression of the disease.

XII. EXAMPLES

Example 1

Discovery of Biomarkers for Alzheimer's Disease

Materials and Methods

Study design and clinical samples: CSF samples (150 µl) from 97 Alzheimer's disease patients (age: Mean 74.11, Range 50-89) including 83 very mild cases with a Mini-Mental State Examination (MMSE) of >24 and 49 Normal individuals (age: Mean 62.94, Range 39-92) were used in this study (see Table 3).

TABLE 3

Clinical Characteristics

| Diagnosis | No | Gender (M:F) | Age (y) | MMSE score |
|---|---|---|---|---|
| Probable AD | 97 | 27:70 | 74.1 (7.4) | 24.9 (3.8) |
| Normal | 49 | 22:27 | 62.9 (12.8) | 28.3 (2.4) |

Values are means (SD).

All patients underwent a thorough clinical investigation that included the following: medical (including history); physical, neurological, and psychiatric examinations; screening laboratory tests; an electroencephalogram; and a computerized tomography scan of the brain. The presence or absence of dementia was diagnosed according to DSM-IV criteria. Probable AD was diagnosed according to NINCDS-ADRDA criteria (McKhann G. et al. (1984) *Neurology* 34:939-944) and disease severity was assessed using MMSE scores (Folstein M F et al., (1975) *J Psychiatr Res* 12:189-198).

CSF samples were obtained by lumbar puncture in the L3/L4 or L4/L5 interspace, collected in polypropylene tubes and stored at −80° C. All patients (or their nearest relatives) and normal individuals gave informed consent to participate in the study, which was conducted according to the Helsinki Declaration. The CSF samples were sourced through three specialized centers at Piteå River Valley Hospital in Sweden (AD site 1, N=64), University of Kuopio in Finland (AD site 2, N=33) and University of Gottenburg in Sweden (Normal, N=49). The samples along with pooled reference CSF were aliquoted into 96-well microtiter plates with randomized placement to help eliminate systematic bias.

SELDI analysis: Clinical CSF samples were thawed, and 5 µl of each sample was diluted into 50 µl of the appropriate binding buffer and profiled on a range of ProteinChip® Array types (Ciphergen Biosystems, Fremont, Calif.). All array preparation was performed using a Biomek® 2000 robot (Beckman Coulter) with an integrated shaker and randomized sample placement. The following binding buffers were used for each ProteinChip Array type: 10% acetonitrile with 0.1% trifluoroacetic acid for H50 arrays, 100 mM Sodium Phosphate (pH 7.0, 0.5 M NaCl) for IMAC30-Cu arrays, 100 mM Sodium Acetate (pH 4.0) for CM10 arrays, and 100 mM Tris (pH 9.0) for Q10 arrays. The samples were allowed to bind for 30 minutes at room temperature. Each array was washed three times with the appropriate binding buffer and rinsed twice with water before the addition of Energy Absorbing Molecules (EAM) used for facilitating desorption and ionization of proteins in the mass spectrometer reader. Sinapinic Acid (SPA) and 4-hydroxy-alpha-cyanocinnamic acid (CHCA) were used as EAMs (Ciphergen Biosystems, Fremont, Calif.). The arrays with SPA were read at two different instrument settings to focus on lower and higher masses while CHCA readings focused on the lower mass region (the VGF peptide in Table 1 was identified using a high energy instrument setting). Each sample was run in triplicate on separate arrays on successive days. Analysis of the arrays was performed in a ProteinChip Reader, series PBS (IIc) (Ciphergen Biosystems, Fremont, Calif.). A protein retentate map was generated in which the individual proteins were displayed as unique peaks based on their mass and charge (m/z).

To ensure reproducibility of sample preparation and array analysis, a reference CSF standard was randomly distributed in several separate aliquots among the clinical samples and analyzed under exactly the same conditions. Reproducibility was measured as pooled coefficients of variation (CV) for each set of acquisition parameters. The CV values were determined to be 20-25% (N=28) and were independent of array lot.

Data Analysis: ProteinChip profiling spectral data were collected using ProteinChip Software version 3.1 and directly exported to CiphergenExpress™ Software version 3.0, where data handling and univariate analysis were performed. All spectra were mass calibrated internally and peak intensities were normalized. Peak clustering was performed in a range that excluded the very low mass region, which is dominated by EAM peaks. P values for individual peaks across each group were calculated using a Mann-Whitney test. The AUC of the receiver operator characteristic curve (ROC AUC) was calculated for each peak and the number of features reduced by keeping only peaks with values above 0.65. All peaks showing a significant difference in the initial univariate analysis were checked manually to exclude any spurious peaks. For further data reduction, the AD samples were compared separately by site, i.e., Swedish (AD site 1) vs. healthy controls and Finnish (AD site 2) vs. healthy controls, to select candidate biomarkers with ROC AUC values above 0.65 in both comparisons and changed in the same direction.

Marker purification and ID: Biomarkers were purified using combinations of chromatographic techniques employing a range of Biosepra sorbents typically followed by SDS-PAGE. The purification schemes were monitored using a ProteinChip Reader to track biomarkers of interest. For proteins smaller than 30 kDa, intact bands of interest were extracted from gels and reanalyzed using the ProteinChip Reader to confirm their exact masses matched with the original biomarker. The gel-extracted proteins were in-solution digested with trypsin and proteins larger than 30 kDa were in-gel digested. Tryptic digests were analyzed by peptide mapping using the ProteinChip Reader and by tandem MS using a Q-STAR (Applied Biosystems) instrument fitted with a PCI-1000 ProteinChip Interface. Biomarkers smaller than 4 kDa were enriched by combinations of chromatographic techniques and identified directly by tandem MS without SDS-PAGE purification and/or trypsin digestion.

The techniques described in the preceding paragraph allowed the identification of the VGF peptide biomarker of Table 1.

The VGF peptide of Table 1 is derived from the neurosecretory protein VGF described in the Swiss Protein Database as VGF_HUMAN (O15240) (amino acids 23 to 616). The deposited sequence appears below (SEQ ID NO:2):

```
  1 MKALRLSASA LFCLLLINGLGAAPPGRPEA QPPPLSSEHK EPVAGDAVPG PKDGSAPEVR   60
 61 GARNSEPQDE GELFQGVDPR ALAAVLLQAL DRPASPPAPS GSQQGPEEEA AEALLTETVR  120
121 SQTHSLPAAG EPEPAAPPRP QTPENGPEAS DPSEELEALA SLLQELRDFS PSSAKRQQET  180
181 AAAETETRTH TLTRVNLESP GPERVWRASW GEFQARVPER APLPPPAPSQ FQARMPDSGP  240
```

```
241 LPETHKFGEG VSSPKTHLGE ALAPLSKAYQ GVAAPFPKAR RAESALLGGS EAGERLLQQG  300

301 LAQVEAGRRQ AEATRQAAAQ EERLADLASD LLLQYLLQGG ARQRGLGGRG LQEAAEERES  360

361 AREEEEAEQE RRGGEERVGE EDEEAAEAAE AEADEAERAR QNALLFAEEE DGEAGAEDKR  420

421 SQEETPGHRR KEAEGTEEGG EEEDDEEMDP QTIDSLIELS TKLHLPADDV VSIIEEVEEK  480

481 RNRKKKAPPE PVPPPRAAPA PTHVRSPQPP PPPPSARDEL PDWNEVLPPW DREEDEVYPP  540

541 GPYHPFPNYI RPRTLQPPSA LRRRHYHHAL PPSRHYPGRE AQARHAQQEE AEAEERRLQE  600

601 QEELENYIEH VLLRRP
```

The peptide corresponding to the 6620 Da biomarker is underlined (amino acids 421-479; theoretical MW 6621.98, pI 3.98) (SEQ ID NO. 1). The sequenced tryptic peptides are highlighted in bold. This peptide is likely excised from the precursor by prohormone convertases at -KR- cleavage sites, as observed for other peptides derived from secretogranins and chromogranins. Neurosecretory protein VGF is transcribed solely in subpopulations of neuroendocrine cells in vivo and it is induced by neurotrophins in target cells in vitro (Canu N et al., Genomics. 1997 Oct. 15; 45(2):443-6); Levi A et al., Cell Mol Neurobiol. 2004 August; 24(4):517-33)).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for qualifying Alzheimer's disease status in a subject comprising:
    (a) measuring the concentration of a VGF peptide-1 consisting of the amino acid sequence of SEQ ID NO:1 in cerebral spinal fluid (CSF) from the subject; and
    (b) correlating the the concentration of the VGF peptide-1 with Alzheimer's disease status, wherein an increased CSF concentration of the VGF peptide-1 is indicative of Alzheimer's disease.

2. The method of claim 1, wherein the VGF peptide-1 is measured by capturing the VGF peptide-1 on an adsorbent surface of a SELDI probe and detecting the captured VGF peptide-1 by laser desorption-ionization mass spectrometry.

3. The method of claim 2, wherein the adsorbent is an anion-exchange adsorbent.

4. The method of claim 2, wherein the adsorbent is a biospecific adsorbent.

5. The method of claim 1, wherein VGF peptide-1 is measured by a method that does not involve measuring the mass of VGF peptide-1.

6. The method of claim 5, wherein the method involves an immunoassay.

7. The method of claim 1, wherein the correlating is performed by a software classification algorithm.

8. The method of claim 1, wherein Alzheimer's disease status is selected from Alzheimer's disease and non-Alzheimer's disease.

9. The method of claim 1, further comprising: (c) reporting the status to the subject.

10. The method of claim 1, further comprising: (c) recording the status on a tangible medium.

11. The method of claim 1, further comprising: (c) managing subject treatment based on the status.

12. The method of claim 11, further comprising: (d) measuring VGF peptide-1 after subject management and correlating the measurement with disease progression.

13. The method of claim 11, wherein, the measurement correlates with Alzheimer's disease, and the managing subject treatment comprises administering a cholinesterase inhibitor to the subject.

14. The method of claim 1, further comprising: (c) measuring the VGF peptide-1 after subject management and correlating the measurement with disease progression.

15. A method for determining the course of Alzheimer's disease comprising:
    (a) measuring the CSF concentration of a VGF peptide-1 consisting of the amino acid sequence of SEQ ID NO: 1 in a subject sample at a first time;
    (b) measuring the CSF concentration of the VGF peptide-1 in a subject sample at a second time; and
    (c) comparing the first measurement and the second measurement; wherein an increased CSF concentration of the VGF peptide-1 in the second measurement indicates progression of Alzheimer's disease.

* * * * *

```
                        SEQUENCE LISTING

<160> NUMBER OF SEQ ID NOS: 2

<210> SEQ ID NO 1
<211> LENGTH: 59
<212> TYPE: PRT
<213> ORGANISM: Homo sapiens
<220> FEATURE:
<223> OTHER INFORMATION: VGF peptide-1, Alzheimer's Disease biomarker
      fragment of neurosecretory protein VGF, VGF amino
      acids 421-479

<400> SEQUENCE: 1

Ser Gln Glu Glu Thr Pro Gly His Arg Arg Lys Glu Ala Glu Gly Thr
 1               5                  10                  15

Glu Glu Gly Gly Glu Glu Glu Asp Asp Glu Glu Met Asp Pro Gln Thr
            20                  25                  30

Ile Asp Ser Leu Ile Glu Leu Ser Thr Lys Leu His Leu Pro Ala Asp
        35                  40                  45

Asp Val Val Ser Ile Ile Glu Glu Val Glu Glu
    50                  55

<210> SEQ ID NO 2
<211> LENGTH: 616
<212> TYPE: PRT
<213> ORGANISM: Homo sapiens
<220> FEATURE:
<223> OTHER INFORMATION: neurosecretory protein VGF, nerve growth factor
      (NGF) inducible protein

<400> SEQUENCE: 2

Met Lys Ala Leu Arg Leu Ser Ala Ser Ala Leu Phe Cys Leu Leu Leu
 1               5                  10                  15

Ile Asn Gly Leu Gly Ala Ala Pro Pro Gly Arg Pro Glu Ala Gln Pro
            20                  25                  30

Pro Pro Leu Ser Ser Glu His Lys Glu Pro Val Ala Gly Asp Ala Val
        35                  40                  45
```

```
Pro Gly Pro Lys Asp Gly Ser Ala Pro Glu Val Arg Gly Ala Arg Asn
    50                  55                  60
Ser Glu Pro Gln Asp Glu Gly Glu Leu Phe Gln Gly Val Asp Pro Arg
65                  70                  75                  80
Ala Leu Ala Ala Val Leu Leu Gln Ala Leu Asp Arg Pro Ala Ser Pro
                85                  90                  95
Pro Ala Pro Ser Gly Ser Gln Gln Gly Pro Glu Glu Ala Ala Glu
            100                 105                 110
Ala Leu Leu Thr Glu Thr Val Arg Ser Gln Thr His Ser Leu Pro Ala
            115                 120                 125
Ala Gly Glu Pro Glu Pro Ala Ala Pro Arg Pro Gln Thr Pro Glu
130                 135                 140
Asn Gly Pro Glu Ala Ser Asp Pro Ser Glu Leu Glu Ala Leu Ala
145                 150                 155                 160
Ser Leu Leu Gln Glu Leu Arg Asp Phe Ser Pro Ser Ala Lys Arg
                165                 170                 175
Gln Gln Glu Thr Ala Ala Ala Glu Thr Glu Thr Arg Thr His Thr Leu
            180                 185                 190
Thr Arg Val Asn Leu Glu Ser Pro Gly Pro Glu Arg Val Trp Arg Ala
        195                 200                 205
Ser Trp Gly Glu Phe Gln Ala Arg Val Pro Glu Arg Ala Pro Leu Pro
    210                 215                 220
Pro Pro Ala Pro Ser Gln Phe Gln Ala Arg Met Pro Asp Ser Gly Pro
225                 230                 235                 240
Leu Pro Glu Thr His Lys Phe Gly Gly Val Ser Ser Pro Lys Thr
                245                 250                 255
His Leu Gly Glu Ala Leu Ala Pro Leu Ser Lys Ala Tyr Gln Gly Val
            260                 265                 270
Ala Ala Pro Phe Pro Lys Ala Arg Arg Ala Glu Ser Ala Leu Leu Gly
        275                 280                 285
Gly Ser Glu Ala Gly Glu Arg Leu Leu Gln Gln Gly Leu Ala Gln Val
    290                 295                 300
Glu Ala Gly Arg Arg Gln Ala Glu Ala Thr Arg Gln Ala Ala Gln
305                 310                 315                 320
Glu Glu Arg Leu Ala Asp Leu Ala Ser Asp Leu Leu Leu Gln Tyr Leu
                325                 330                 335
Leu Gln Gly Gly Ala Arg Gln Arg Gly Leu Gly Gly Arg Gly Leu Gln
            340                 345                 350
Glu Ala Ala Glu Glu Arg Glu Ser Ala Arg Glu Glu Glu Ala Glu
            355                 360                 365
Gln Glu Arg Arg Gly Gly Glu Glu Arg Val Gly Glu Glu Asp Glu Glu
        370                 375                 380
Ala Ala Glu Ala Ala Glu Ala Glu Ala Asp Glu Ala Glu Arg Ala Arg
385                 390                 395                 400
Gln Asn Ala Leu Leu Phe Ala Glu Glu Glu Asp Gly Glu Ala Gly Ala
                405                 410                 415
Glu Asp Lys Arg Ser Gln Glu Glu Thr Pro Gly His Arg Arg Lys Glu
            420                 425                 430
Ala Glu Gly Thr Glu Glu Gly Gly Glu Glu Glu Asp Glu Glu Met
            435                 440                 445
Asp Pro Gln Thr Ile Asp Ser Leu Ile Glu Leu Ser Thr Lys Leu His
    450                 455                 460
```

-continued

```
Leu Pro Ala Asp Asp Val Val Ser Ile Ile Glu Glu Val Glu Glu Lys
465                 470                 475                 480

Arg Asn Arg Lys Lys Lys Ala Pro Pro Glu Pro Val Pro Pro Pro Arg
                485                 490                 495

Ala Ala Pro Ala Pro Thr His Val Arg Ser Pro Gln Pro Pro Pro Pro
            500                 505                 510

Pro Pro Ser Ala Arg Asp Glu Leu Pro Asp Trp Asn Glu Val Leu Pro
        515                 520                 525

Pro Trp Asp Arg Glu Glu Asp Glu Val Tyr Pro Pro Gly Pro Tyr His
        530                 535                 540

Pro Phe Pro Asn Tyr Ile Arg Pro Arg Thr Leu Gln Pro Pro Ser Ala
545                 550                 555                 560

Leu Arg Arg Arg His Tyr His His Ala Leu Pro Pro Ser Arg His Tyr
                565                 570                 575

Pro Gly Arg Glu Ala Gln Ala Arg His Ala Gln Gln Glu Glu Ala Glu
            580                 585                 590

Ala Glu Glu Arg Arg Leu Gln Glu Gln Glu Glu Leu Glu Asn Tyr Ile
        595                 600                 605

Glu His Val Leu Leu Arg Arg Pro
610                 615
```